United States Patent [19]

Okumura et al.

[11] Patent Number: 4,507,512

[45] Date of Patent: Mar. 26, 1985

[54] PROCESS FOR HYDRATION OF OLEFINS

[75] Inventors: Yoshiharu Okumura, Tokyo; Setsuo Kamiyama, Saitama; Hiroshi Furukawa, Saitama; Katsumi Kaneko, Saitama, all of Japan

[73] Assignee: Toa Nenryo Kogyo Kabushiki Kaisha, Tokyo, Japan

[21] Appl. No.: 610,045

[22] Filed: May 14, 1984

[30] Foreign Application Priority Data

May 31, 1983 [JP] Japan .................. 58-94894
Jun. 6, 1983 [JP] Japan .................. 58-99482

[51] Int. Cl.$^3$ .................. C07C 29/04; C07C 31/10; C07C 31/12; C07C 31/135

[52] U.S. Cl. .................. 568/897; 502/64; 502/71; 502/77; 502/78; 568/715; 568/821; 568/835; 568/838; 568/839; 568/899

[58] Field of Search .............. 568/897, 899, 839, 838, 568/835, 821, 715

[56] References Cited

U.S. PATENT DOCUMENTS

| | | | |
|---|---|---|---|
| 2,658,924 | 11/1953 | Lukasiewicz et al. | 568/897 |
| 2,663,744 | 12/1953 | Lukasiewicz et al. | 568/897 |
| 3,173,855 | 3/1965 | Misle et al. | 568/897 |
| 3,194,829 | 7/1965 | Moore et al. | 568/897 |
| 3,493,518 | 2/1970 | Jonassen et al. | 568/897 |
| 3,692,470 | 9/1972 | Ciric | 423/328 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,965,207 | 6/1976 | Weinstein | 260/671 |
| 3,972,983 | 8/1976 | Ciric | 423/328 |
| 4,016,245 | 4/1977 | Plank et al. | 423/328 |
| 4,046,859 | 11/1977 | Plank et al. | 423/328 |
| 4,076,842 | 2/1978 | Plank et al. | 423/328 |
| 4,214,107 | 7/1980 | Chang et al. | 568/897 |
| 4,270,011 | 5/1981 | Okumura et al. | 568/899 |
| 4,284,831 | 8/1981 | Okumura et al. | 568/899 |
| 4,358,626 | 11/1982 | Okumura et al. | 568/899 |

FOREIGN PATENT DOCUMENTS

| | | | |
|---|---|---|---|
| 57-70828 | 1/1982 | Japan . | |
| 826244 | 1/1982 | Japan . | |
| 124723 | 7/1983 | Japan | 568/897 |
| 1297256 | 11/1972 | United Kingdom . | |
| 1334243 | 10/1973 | United Kingdom . | |
| 1518461 | 7/1978 | United Kingdom . | |

*Primary Examiner*—J. E. Evans
*Attorney, Agent, or Firm*—Rebecca Yablonsky

[57] ABSTRACT

An improved process for producing an alcohol by hydrating an olefin wherein the improvement comprises hydrating an olefin in the presence of a hydrogen-type catalyst having a silica/alumina molar ratio of 20 to 500 and a solvent using either:

A. hydrogen-type mordenite or hydrogen-type zeolite Y, and a sulfone; or

B. hydrogen-type crystalline aluminosilicate in which the entrance of the main void is formed by a 10-membered or 12-membered oxygen ring, and a $C_2$ to $C_5$ oxy acid or the lactones, lactides, methyl or ethyl esters thereof.

14 Claims, No Drawings

PROCESS FOR HYDRATION OF OLEFINS

FIELD OF THE INVENTION

The present invention relates to a process for hydrating an olefin. More particularly, it relates to a process for hydrating an olefin such as propylene and butene in the presence of a specific solid catalyst and a specific solvent, thereby producing the corresponding alcohol.

BACKGROUND OF THE INVENTION

Heretofore various catalysts have been known for the hydration of olefins, and attempts have been made to use solid catalysts because of their ease of separation and recovery from the reaction product. Usually the hydration of an olefin is favored when the temperature is low and the pressure is high. However, such a reaction condition is not practical because the known solid catalysts such as silica, alumina, silica-alumina, mordenite, and zeolite become deactivated by liquid water which is formed in the reaction system.

On the other hand, a hydration process is known which employs a cation-exchange resin such as sulfonated styrene-divinylbenzene copolymer as a catalyst. This catalyst exhibits a comparatively high activity for hydration under the condition where there is liquid water. However, it has a drawback. Namely, it irreversibly liberates sulfonic acid groups and becomes greatly deactivated when the reaction temperature is increased, say, above 120° C., so as to obtain the industrially desirable reaction rate. The liberated sulfonic acid groups corrode the apparatus. The deactivated catalyst cannot be regenerated by calcination which is commonly employed for inorganic solid catalysts.

Under these circumstances, there has recently been proposed a process for hydrating an olefin by using a specific crystalline alumino-silicate. (U.S. Pat. No. 4,214,107, and Japanese Patent Laid-open No. 70828/1982.) The proposed process, however, is not practical because the catalyst does not have a sufficiently high catalytic activity. See also Japanese Laid-open No. 826244.

Attempts have been made to perform hydration with a solid catalyst in the presence of a solvent in order to improve the efficiency of hydration. A known solvent for such a purpose is a sulfone-containing solution, see Japanese Patent Laid-open Nos. 10802/1982 and 7605/1978 and equivalent British Pat. No. 1,518,461 and U.S. Pat. No. 4,270,011. It has also been proposed to use an oxy acid or derivative thereof as a solvent, see U.S. Pat. Nos. 4,358,626 and 4,284,831 incorporated by reference. In these processes, the solid catalyst is substantially a cation-exchange resin, and they suffer from disadvantages inherent in the use of a cation-exchange resin.

It is an object of this invention to provide a process for hydrating an olefin with a highly active solid catalyst/solvent combination. Applicants have found that this object can be achieved by using as a catalyst hydrogen-type mordenite or hydrogen-type zeolite Y having a specific silica/alumina ratio in the presence of a sulfone or by using as a catalyst hydrogen-type crystalline aluminosilicate having a specific crystal structure and said specific silica/alumina ratio in the presence of an oxy acid or derivative thereof.

SUMMARY OF THE INVENTION

The gist of this invention resides in an improved process for producing an alcohol by hydrating an olefin, wherein the improvement comprises hydrating an olefin in the presence of hydrogen-type mordenite or hydrogen-type zeolite Y each having a silica/alumina molar ratio of 20 to 500, and a sulfone; or in the presence of hydrogen-type crystalline alumino-silicate and an oxy acid or a derivative thereof, said aluminosilicate being such that the entrance of the main void is formed by a 10-membered or 12-membered oxygen ring and the silica/alumina molar ratio is 20 to 500.

DETAILED DESCRIPTION

Hydration Catalyst

The catalyst used in the hydration process of this invention comprises hydrogen-type crystalline aluminosilicate of such structure that the entrance of the main void is formed by a 10-membered or 12-membered oxygen ring and the silica/alumina molar ratio is 20 to 500.

Examples of the crystalline aluminosilicate used in this invention are described below.

(1) Mordenite

Mordenite occurs naturally and it can also be synthesized. It has a structure such that the entrance of the main void is formed by a 12-membered oxygen ring, and has a silica/alumina molar ratio of 10 as shown in the following formula:

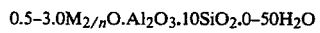

$$0.5-3.0 M_{2/n}O \cdot Al_2O_3 \cdot 10SiO_2 \cdot 0-50H_2O$$

(wherein M is an alkali metal or alkaline earth metal, and n is a valence of metal M.)

The hydration catalyst used in this invention comprises hydrogen-type mordenite obtained by treating mordenite so that the silica/alumina molar ratio is raised to 20 to 500. The treatment includes dealkalization, acid extraction, and steam treatment, which are used in combination with one another.

The dealkalization involves replacing a part or all of the alkali metal or alkaline earth metal in mordenite with hydrogen ions. It is this process which produces the so called hydrogen-type mordenite. Usually the dealkalization is accomplished by treating natural mordenite or synthetic mordenite with an aqueous solution of a water soluble ammonium salt such as ammonium chloride, ammonium nitrate, ammonium sulfate, or ammonium acetate, so that the above-mentioned metal cations in mordenite are replaced by ammonium ions, and then calcining the treated mordenite. The dealkalization is accomplished also by treating natural mordenite or synthetic mordenite with an aqueous solution of an acid such as hydrochloric acid, sulfuric acid, or nitric acid, so that the above mentioned metal cations in mordenite are replaced by hydrogen ions. Dealkalization, however, is not necessarily required, because hydrogen-type mordenite is commercially available and it can be synthesized.

The acid extraction is accomplished by bringing mordenite into contact with a mineral acid such as hydrochloric acid, sulfuric acid, nitric acid or phosphoric acid, or an organic acid such as acetic acid or formic acid, so that alumina in the mordenite is extracted. The contact with the acid should preferably be carried out at 20° to 120° C. for 1 to 100 hours. The acid extraction may be carried out twice or more. The acid extraction may also serve as the above mentioned dealkalization. It is desirable that the content of alkali metal or alkaline earth metal in mordenite be reduced to 0.1 wt.% or less (in terms of metal oxide) by the dealkalization and acid extraction.

The steam treatment which can be combined with the acid extraction may be carried out by heating mordenite at 150° to 800° C., preferably 300° to 700° C., for 0.5 to 50 hours, preferably 1 to 30 hours, in the presence of steam.

By using the above described method, it is possible to raise the silica/alumina ratio to 20 to 500. The catalyst having a silica/alumina ratio of 30 to 400 produces a good effect in this invention.

The mordenite used in this invention exhibits the X-ray diffraction pattern as shown in Table 1.

TABLE 1

| Lattice plane space d (Å) | Relative intensity | Lattice plane space d (Å) | Relative intensity |
|---|---|---|---|
| 13.59 ± 0.2 | S | 4.51 ± 0.02 | S |
| 10.16 ± 0.2 | S | 3.97 ± 0.02 | VS |
| 9.15 ± 0.1 | VS | 3.46 ± 0.01 | VS |
| 6.55 ± 0.05 | S | 3.37 ± 0.01 | S |
| 5.80 ± 0.05 | S | 3.22 ± 0.01 | S |

Note:
VS: Very Strong,
S: Strong

(2) Zeolite Y

Zeolite Y is a synthetic zeolite of faujasite type. It forms the 12-membered oxygen ring. The hydration catalyst is prepared by removing by extraction alkali metal or alkaline earth metal and alumina so that the above-mentioned silica/alumina ratio is established.

The dealkalization and the removal of alumina are accomplished by bringing zeolite Y into contact with silicon tetrachloride. To be more specific, zeolite Y is dehydrated and dried at 300° to 500° C. and then brought into contact with the vapor of silicon tetrachloride, while being heated from room temperature to 400° to 600° C. This treatment increases the silica/alumina ratio. If it is desirable to increase the silica/alumina ratio further, this treatment may be combined with the above mentioned acid extraction and steam treatment. It is desirable that the content of alkali metal or alkaline earth metal in zeolite Y be 0.1 wt.% or less, and the silica/alumina ratio be 30 to 400.

The hydrogen-type zeolite Y used in this invention exhibits the X-ray diffraction pattern as shown in Table 2.

TABLE 2

| Lattice plane space d (Å) | Relative intensity | Lattice plane space d (Å) | Relative intensity |
|---|---|---|---|
| 14.71 ± 0.2 | VS | 3.410 ± 0.07 | W |
| 8.83 ± 0.2 | S | 3.276 ± 0.07 | S |
| 7.43 ± 0.2 | S | 2.976 ± 0.07 | W |
| 5.71 ± 0.1 | S | 2.873 ± 0.07 | M |
| 4.71 ± 0.1 | M | 2.820 ± 0.07 | S |
| 4.33 ± 0.1 | S | 2.720 ± 0.05 | W |
| 3.86 ± 0.1 | W | 2.655 ± 0.05 | W |
| 3.734 ± 0.07 | S | 2.597 ± 0.05 | M |

Note:
M: Medium,
W: Weak

(3) Synthetic aluminosilicate (a)

Synthetic aluminosilicate (a) has a composition as shown by the following formula:

$$0.7 - 1.1 M_{2/n}O \cdot Al_2O_3 \cdot 5 - 300 SiO_2 \cdot 0 - 40 H_2O$$

(wherein M is a metal cation and n is the valence of the cation.) The entrance of the main void is formed by a 10-membered or 12-membered oxygen ring.

Crystalline aluminosilicate like this is known and it can be prepared by heating a mixture of aluminum compound (e.g., aluminum sulfate), silicon compound (e.g., sodium silicate), mineral acid (e.g., sulfuric acid), salt of metal cation (e.g., sodium chloride), cationic organic nitrogen compound (e.g., tetrapropylammonium bromide), and water.

Examples of synthetic aluminosilicate (a) include ZSM-5, ZSM-11, ZSM-12, ZSM-23, ZSM-35, and ZSM-38, in which the entrance of the main void is formed by a 10-membered oxygen ring, and ZSM-4, ZSM-10, ZSM-20, and ZSM-43 in which the entrance of the main void is formed by a 12-membered oxygen ring. They are products developed by Mobile Oil Co. These products exhibit the X-ray diffraction patterns as shown in Tables 3 to 13. They are described in detail in the following U.S. patents, British patents, and Japanese Laid-open patents.

| | |
|---|---|
| ZSM-5 | U.S. Pat. No. 3,702,886 |
| ZSM-8 | British Patent 1,334,243 |
| ZSM-11 | U.S. Pat. No. 3,709,979 |
| ZSM-12 | U.S. Pat. No. 3,832,449 |
| ZSM-23 | U.S. Pat. No. 4,076,842 |
| ZSM-35 | U.S. Pat. No. 4,016,245 |
| ZSM-38 | U.S. Pat. No. 4,046,859 |
| ZSM-4 | British 1,297,256 |
| ZSM-10 | U.S. Pat. No. 3,692,470 |
| ZSM-20 | U.S. Pat. No. 3,972,983 |
| ZSM-43 | Japanese 68800/1979 |

TABLE 3

(ZSM-5)

| Lattice plane space d (Å) | Relative intensity | Lattice plane space d (Å) | Relative intensity |
|---|---|---|---|
| 11.3 ± 0.3 | S | 4.63 ± 0.1 | W |
| 10.2 ± 0.3 | S | 4.28 ± 0.1 | W |
| 7.5 ± 0.3 | W | 3.86 ± 0.1 | VS |
| 7.1 ± 0.2 | W | 3.75 ± 0.05 | S |
| 6.04 ± 0.2 | W | 3.63 ± 0.05 | M |
| 5.75 ± 0.1 | W | 3.06 ± 0.05 | W |
| 5.61 ± 0.1 | W | 3.00 ± 0.05 | S |
| 5.03 ± 0.1 | W | | |

TABLE 4

(ZSM-8)

| Lattice plane space d (Å) | Relative intensity | Lattice plane space d (Å) | Relative intensity |
|---|---|---|---|
| 11.1 ± 0.2 | S | 5.01 ± 0.1 | W |
| 10.0 ± 0.2 | S | 4.26 ± 0.08 | M |
| 7.4 ± 0.15 | W | 4.08 ± 0.08 | M |
| 7.1 ± 0.15 | W | 3.85 ± 0.07 | VS |
| 6.4 ± 0.1 | W | 3.71 ± 0.05 | M |
| 6.02 ⎫ ⎬ ± 0.1 5.98 ⎭ | W | 3.47 ± 0.04 | W |
| | | 3.05 ± 0.03 | W |
| 5.57 ± 0.1 | W | | |

TABLE 5

(ZSM-11)

| Lattice plane space d (Å) | Relative intensity | Lattice plane space d (Å) | Relative intensity |
|---|---|---|---|
| 11.2 ± 0.2 | M | 4.39 ± 0.08 | W |
| 10.1 ± 0.2 | M | 3.86 ± 0.07 | VS |
| 6.73 ± 0.2 | W | 3.73 ± 0.07 | M |
| 5.75 ± 0.1 | W | 3.49 ± 0.07 | W |
| 5.61 ± 0.1 | W | (3.07, 3.00) ± 0.05 | W |
| 5.03 ± 0.1 | W | 2.01 ± 0.02 | W |
| 4.62 ± 0.1 | W | | |

TABLE 6

(ZSM-12)

| Lattice plane space d (Å) | Relative intensity | Lattice plane space d (Å) | Relative intensity |
|---|---|---|---|
| 11.9 ± 0.2 | M | 3.49 ± 0.07 | W |
| 10.1 ± 0.2 | M | 3.38 ± 0.07 | M |
| 4.76 ± 0.1 | W | 3.20 ± 0.06 | W |
| 4.29 ± 0.08 | VS | 3.05 ± 0.05 | W |
| 3.98 ± 0.08 | M | 2.54 ± 0.03 | W |
| 3.87 ± 0.07 | VS | | |

TABLE 7

(ZSM-23)

| Lattice plane space d (Å) | Relative intensity | Lattice plane space d (Å) | Relative intensity |
|---|---|---|---|
| 11.2 ± 0.23 | M | 3.44 ± 0.07 | S |
| 10.1 ± 0.20 | W | 3.36 ± 0.07 | W |
| 7.87 ± 0.15 | W | 3.16 ± 0.07 | W |
| 5.59 ± 0.10 | W | 3.05 ± 0.06 | W |
| 5.44 ± 0.10 | W | 2.99 ± 0.06 | W |
| 4.90 ± 0.10 | W | 2.85 ± 0.06 | W |
| 4.53 ± 0.10 | S | 2.54 ± 0.05 | M |
| 3.90 ± 0.08 | VS | 2.47 ± 0.05 | W |
| 3.72 ± 0.08 | VS | 2.40 ± 0.05 | W |
| 3.62 ± 0.07 | VS | 2.34 ± 0.05 | W |
| 3.54 ± 0.07 | M | | |

TABLE 8

(ZSM-35)

| Lattice plane space d (Å) | Relative intensity | Lattice plane space d (Å) | Relative intensity |
|---|---|---|---|
| 9.6 ± 0.20 | VS | 3.54 ± 0.07 | VS |
| 7.10 ± 0.15 | M | 3.48 ± 0.07 | VS |
| 6.98 ± 0.14 | M | 3.39 ± 0.07 | VS |
| 6.64 ± 0.14 | M | 3.32 ± 0.07 | W-M |
| 5.78 ± 0.12 | W | 3.14 ± 0.06 | W-M |
| 5.68 ± 0.12 | W | 2.90 ± 0.06 | W |
| 4.97 ± 0.10 | W | 2.85 ± 0.06 | W |
| 4.58 ± 0.09 | W | 2.71 ± 0.05 | W |
| 3.99 ± 0.08 | S | 2.65 ± 0.05 | W |
| 3.94 ± 0.08 | M-S | 2.62 ± 0.05 | W |
| 3.85 ± 0.08 | M | 2.58 ± 0.05 | W |
| 3.78 ± 0.08 | S | 2.54 ± 0.05 | W |
| 3.74 ± 0.08 | W | 2.48 ± 0.05 | W |
| 3.66 ± 0.07 | M | | |

TABLE 9

(ZSM-36)

| Lattice plane space d (Å) | Relative intensity | Lattice plane space d (Å) | Relative intensity |
|---|---|---|---|
| 9.8 ± 0.20 | S | 3.57 ± 0.07 | VS |
| 9.1 ± 0.19 | M | 3.51 ± 0.07 | VS |
| 8.0 ± 0.16 | W | 3.34 ± 0.07 | M |
| 7.1 ± 0.14 | M | 3.17 ± 0.06 | S |

TABLE 9-continued (ZSM-36)

| Lattice plane space d (Å) | Relative intensity | Lattice plane space d (Å) | Relative intensity |
|---|---|---|---|
| 6.7 ± 0.14 | M | 3.08 ± 0.06 | M |
| 6.0 ± 0.12 | W | 3.00 ± 0.06 | W |
| 5.0 ± 0.10 | W | 2.92 ± 0.06 | M |
| 4.37 ± 0.09 | W | 2.73 ± 0.06 | W |
| 4.23 ± 0.09 | W | 2.66 ± 0.05 | W |
| 4.01 ± 0.08 | VS | 2.60 ± 0.05 | W |
| 3.81 ± 0.08 | VS | 2.49 ± 0.05 | W |
| 3.69 ± 0.07 | M | | |

TABLE 10

(ZSM-4)

| Lattice plane space d (Å) | Relative intensity | Lattice plane space d (Å) | relative intensity |
|---|---|---|---|
| 9.1 ± 0.2 | VS | 3.71 ± 0.05 | M |
| 7.94 ± 0.1 | M-W | 3.63 ± 0.05 | M |
| 6.90 ± 0.1 | M | 3.52 ± 0.05 | S |
| 5.97 ± 0.07 | S | 3.44 ± 0.05 | M |
| 5.50 ± 0.05 | M-W | 3.16 ± 0.05 | S |
| 5.27 ± 0.05 | M-W | 3.09 ± 0.05 | M |
| 4.71 ± 0.05 | M-W | 3.04 ± 0.05 | M |
| 4.39 ± 0.05 | W | 2.98 ± 0.05 | M |
| 3.96 ± 0.05 | W | 2.92 ± 0.05 | S |
| 3.80 ± 0.05 | S | | |

TABLE 11

(ZSM-10)

| Lattice plane space d (Å) | Relative intensity ($I/I_o$) | Lattice plane space d (Å) | Relative intensity ($I/I_o$) |
|---|---|---|---|
| 15.85 | 58 | 3.87 | 91 |
| 13.92 | 42 | 3.64 | 100 |
| 10.22 | 13 | 3.54 | 56 |
| 7.87 | 22 | 3.47 | 25 |
| 7.55 | 56 | 3.42 | 27 |
| 7.04 | 13 | 3.32 | 13 |
| 6.29 | 35 | 3.22 | 16 |
| 5.96 | 22 | 3.16 | 31 |
| 5.46 | 31 | 3.10 | 67 |
| 5.25 | 15 | 3.04 | 73 |
| 5.06 | 25 | 2.89 | 89 |
| 4.50 | 75 | 2.73 | 48 |
| 4.41 | 67 | 2.69 | 15 |
| 4.32 | 27 | 2.57 | 15 |

TABLE 12

(ZSM-20)

| Lattice plane space d (Å) | Relative intensity | Lattice plane space d (Å) | Relative intensity |
|---|---|---|---|
| 14.90 ± 0.3 | VS | 3.45 ± 0.07 | W |
| 14.21 ± 0.3 | VS | 3.33 ± 0.07 | W |
| 8.67 ± 0.2 | M | 3.29 ± 0.07 | M |
| 8.19 ± 0.15 | W | 3.20 ± 0.06 | W |
| 7.44 ± 0.15 | M | 2.90 ± 0.06 | M |
| 5.66 ± 0.10 | S | 2.87 ± 0.06 | W |
| 5.34 ± 0.10 | W | 2.84 ± 0.06 | M |
| 5.17 ± 0.10 | W | 2.79 ± 0.06 | W |
| 5.00 ± 0.10 | W | 2.75 ± 0.06 | W |
| 4.87 ± 0.10 | W | 2.70 ± 0.05 | W |
| 4.74 ± 0.10 | W | 2.61 ± 0.05 | M |
| 4.33 ± 0.09 | M | 2.41 ± 0.05 | W |
| 3.98 ± 0.08 | W | 2.37 ± 0.05 | W |
| 3.83 ± 0.08 | W | 2.17 ± 0.04 | W |
| 3.76 ± 0.08 | M | 2.14 ± 0.04 | W |
| 3.66 ± 0.07 | S | 2.09 ± 0.04 | W |
| 3.60 ± 0.07 | W | 2.05 ± 0.04 | W |
| 3.55 ± 0.07 | W | | |

TABLE 13

| (ZSM-43) | | | |
|---|---|---|---|
| Lattice plane space d (Å) | Relative intensity | Lattice plane space d (Å) | Relative intensity |
| 9.8 ± 0.2 | W | 3.31 ± 0.07 | S |
| 7.6 ± 0.1 | S | 3.21 ± 0.06 | VS |
| 6.8 ± 0.1 | M | 3.06 ± 0.06 | S |
| 8.0 ± 0.1 | W | 2.84 ± 0.06 | M |
| 4.75 ± 0.1 | VS | 2.57 ± 0.05 | W |
| 3.78 ± 0.08 | S | 2.52 ± 0.05 | W |
| 3.52 ± 0.07 | M | | |

The above-mentioned synthetic aluminosilicate (a) usually has the silica/alumina molar ratio as shown by the above formula, but the ratio can be raised by changing the ratio of reagents used in synthesis.

The synthetic aluminosilicate (a) can be easily rendered hydogen-type by dealkalization and acid extraction in the same way as for the above mentioned mordenite.

(4) Synthetic aluminosilicate (b)

Synthetic aluminosilicate (b) has a composition as shown by the following formula:

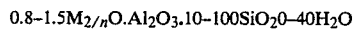

$0.8-1.5M_{2/n}O \cdot Al_2O_3 \cdot 10-100SiO_2 \cdot 0-40H_2O$ (wherein M is a metal cation, and n is the valence of the cation.)

The entrance of the main void is formed by a 10-membered oxygen ring. The aluminosilicate (b) exhibits the X-ray diffraction pattern as shown in Table 14.

TABLE 14

| Lattice Plane Space d (Å) | Relative intensity | Lattice plane space d (Å) | Relative intensity |
|---|---|---|---|
| 11.2 ± 0.2 | S | 3.75 ± 0.05 | S |
| 10.1 ± 0.2 | S | 3.73 ± 0.05 | S |
| 7.5 ± 0.15 | W | 3.65 ± 0.05 | S |
| 6.01 ± 0.01 | M | 3.06 ± 0.05 | M |
| 3.86 ± 0.05 | VS | 3.00 ± 0.05 | M |
| 3.82 ± 0.05 | S | | |

Synthetic aluminosilicate (b) is composed substantially of inorganic materials. It is prepared by heating an aqueous reaction mixture having the following composition:

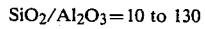

$SiO_2/Al_2O_3 = 10$ to $130$

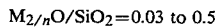

$M_{2/n}O/SiO_2 = 0.03$ to $0.5$

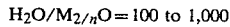

$H_2O/M_{2/n}O = 100$ to $1,000$

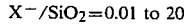

$X^-/SiO_2 = 0.01$ to $20$ (wherein M and n are defined as above, and $X^-$ is an anion of the salt used as a mineralizing agent) at a crystallizing temperature until the crystals of the reaction mixture are formed. (Detailed description is given in Japanese Patent Laid-open No. 45111/1983.)

A desired silica/alumina molar ratio can be obtained by changing the ratio of reagents used in synthesis; but the ratio can be raised by subjecting the alumino-silicate to acid extraction as in the case of the above mentioned mordenite or by bringing the alumino-silicate into contact with carbon tetrachloride as in the case of the above mentioned zeolite Y.

The synthetic aluminosilicate (b) can be easily rendered hydrogen-type by dealkalization or acid extraction in the same way as for the above-mentioned mordenite.

Sulfone

The sulfone used in the process of this invention is a non-cyclic or cyclic sulfone. Examples of non-cyclic sulfones include dimethylsulfone, diethylsulfone, methylethylsulfone, dipropylsulfone, dibutylsulfone, divinylsulfone, sulfonal, and trional. Examples of cyclic sulfones include sulfolane, alkylsubstituted sulfolane (e.g., 2-methylsulfolane, 3-methylsulfolane, 3-propylsulfolane, 3-butylsulfolane, and 2-methyl-4-butylsulfolane), and 3-sulfolene. These sulfones are mostly solid at normal temperature, and they are used in the form of aqueous solutions. In some cases they may be dissolved in a lower alcohol such as methanol or ethanol or in an alcohol which is the desired product of hydration. The above-mentioned sulfones may be used in combination with one another.

Oxyacid and derivatives thereof

The oxyacid includes, for example, hydroxyacetic acid, lactic acid, 3-hydroxypropionic acid, $\beta,\beta,\beta$-trichlorolactic acid, hydroxypivalic acid, and $\gamma$,hydroxybutyric acid. The preferred derivatives of the oxyacid are lactones, which are a self-condensate of oxyacid, and esters of oxyacid. Examples of lactones include $\beta$,propionlactone, $\beta,\beta$-dimethylpropiolactone, $\gamma$-butyolactone, $\gamma$-valerolactone, $\delta$-valerolactone, diglycolide, and lactide. Examples of esters of oxyacid include methyl ester and ethyl ester of glycolic acid.

When in use, the oxy acid and derivatives thereof are dissolved in water, but they may be dissolved in a lower alcohol such as methanol or ethanol, or in an alcohol which is the desired product of the hydration reaction. Two or more kinds of oxy acids or derivatives thereof may be used.

Olefin

The olefin that can be hydrated according to the process of this invention includes linear, branched, and cyclic olefins. It also includes terminal olefins and internal olefins. Suitable olefins are monoolefins of carbon number 2 to 12, preferably 2 to 8. Examples of such monoolefins include ethylene, propylene, 1-butene, 2-butene, isobutene, pentenes, hexenes, heptenes, octenes, cyclobutene, cyclopentene, cyclohexene, methylcyclopentene, methylcyclohexene, cyclooctene, and styrene. The process of this invention can usefully be applied to the hydration of linear alpha or internal monoolefins and cyclic monoolefins of carbon number 2 to 6 such as ethylene, propylene, 1-butene, 2-butene, pentenes, hexenes, and cyclohexene. The above mentioned olefins may be used in combination with one another or with a non-olefinic compound such as an alkane.

Process of hydration

The present invention is intended to react an olefin with water in the presence of the specified hydration catalyst and solvent, thereby producing the corresponding alcohol. The hydration reaction is carried out batchwise or continuously by feeding an olefin and the solvent to a fixed bed or fluidized bed containing the hydration catalyst.

One mole of olefin is brought into contact with 1 to 20 mol of water. The sulfone or oxy acid or derivative thereof is usually used in the form of an aqueous solution. The amount of sulfone is 0.5 to 30 parts by volume, preferably 1 to 20 parts by volume, for 1 part by volume of water. The amount of oxyacid or derivative thereof is 0.2 to 30 parts by volume, preferably 1 to 20 parts by volume, for 1 part by volume of water. The reaction temperature is usually 50° to 300° C., and preferably 100° to 250° C. The reaction pressure is 5 to 200 kg/cm$^2$ which is high enough to maintain the liquid phase or gas-liquid multi-phase in the reaction system. The reaction time is usually 20 minutes to 20 hours in the case of batchwise reaction, and the LHSV is usually 0.1 to 10 in the case of continuous reaction.

It is by this hydration reaction that an olefin is hydrated and converted to the corresponding alcohol. This invention is particularly useful for producing isopropanol from propylene and sec-butanol from 1-butene or 2-butene.

The process of this invention makes it possible to produce alcohol in higher yields than the hydration process that employs a conventional inorganic solid acid. Unlike the hydration process that employs an ion-exchange resin as a catalyst, the process of this invention is not restricted by the hydration temperature and is free of problems caused by the separation of the acid components. The hydration catalyst used in this invention can be regenerated by calcination which is commonly employed for inorganic solid catalysts. The process of this invention produces an alcohol at a high selectivity with a minimum of by-products.

The invention is now described in more detail with reference to the following examples, in which "%" is based on weight, unless otherwise noted.

EXAMPLES 1 TO 5 AND COMPARATIVE EXAMPLES 1 AND 2

Preparation of hydration catalysts

Synthetic mordenite (Zeolon 900Na, a product of Norton Co.) was treated with a 10% aqueous solution of ammonium chloride (15 cc for 1 g of mordenite) at 80° C. for 1.5 hours, and then the aqueous solution was removed. This step was repeated three times. The mordenite was thoroughly washed and dried at 120° C. and finally calcined at 600° C. for 3 hours. Thus there was obtained hydrogen-type mordenite containing 0.1% of Na$_2$O and having a silica/alumina molar ratio (referred to as S/A hereinafter) of 10. This mordenite is designated as catalyst A.

Catalyst A was treated with 12N hydrochloric acid (15 cc for 1 g of catalyst A) at 90° C. for 20 hours. The treated catalyst A was washed with water until chlorine ion was not detected any longer, and then dried at 120° C. and finally calcined at 600° C. for 3 hours in air. Thus there was obtained hydrogen-type mordenite containing 0.04% of Na$_2$O and having an S/A of 31. This mordenite is designated as catalyst B.

Catalyst A was treated with 12N hydrochloric acid (15 cc for 1 g of catalyst A) at 90° C. for 20 hours. The treated catalyst A was treated again with this hydrochloric acid, and then washed with water until chlorine ion was not detected any longer. It was then dried at 120° C. and finally calcined at 600° C. for 3 hours in air. Thus there was obtained hydrogen-type mordenite containing 0.03% of Na$_2$O and having an S/A of 50. This mordenite is designated as catalyst C.

Catalyst C was treated with hot air containing 10% of steam at 700° C. for 3 hours and then treated with 12N hydrochloric acid at 90° C. for 20 hours. The treatment with hydrochloric acid was repeated once again. The treated catalyst C was washed with water, dried, and calcined in the same way as above. Thus there was obtained hydrogen-type mordenite (catalyst D) containing 0.01% of Na$_2$O and having an S/A of 108.

Catalyst D was repeatedly subjected to steam treatment and acid extraction in the same way as above in order to increase the silica/alumina ratio. Thus there were obtained catalysts E to G containing Na$_2$O and having S/A as follows:

Catalyst E (Na$_2$O: 0.01%, S/A: 203)
Catalyst F (Na$_2$O: 0.003%, S/A: 404)
Catalyst G (Na$_2$O: 0.002%. S/A : 550)

The hydration catalysts A to G prepared as above gave the same X-ray diffraction pattern as shown in Table 1. This indicates that the crystal structure of mordenite was not affected by the treatment.

Hydration reaction of olefin

Into a 500-ml stainless steel autoclave equipped with a stirrer were charged 10 ml (6.0 g) of hydration catalyst C prepared as mentioned above, 240 ml of sulfolane, and 60 ml of water, and finally 60 ml (37 g) of 1-butene was forced in under pressure. The hydration reaction was carried out at 140° C., under 40 kg/cm$^2$, for 5 hours. After the reaction was complete, the autoclave was cooled rapidly and unreacted 1-butene was removed. The analysis of the reaction product indicates that sec-butanol (SBA) was formed in a yield of 7.3 mol%. The space-time yield of SBA was 70 g/l-catalyst/hr. The selectivity to SBA was 99 mol%, with the formation of a trace amount of sec-butyl ether and octene as by-products.

Using the catalysts obtained as described above, the hydration reaction of 1-butene was carried out in the same way as described above. The results are shown in Table 15.

TABLE 15

| Example No. | Hydration catalysts designation | Silica/alumina (molar ratio) | Yield of SBA (mol %) | Space-time yield of SBA (g/l/hr) | Selectivity to SBA (mol %) |
|---|---|---|---|---|---|
| Comparative Example 1 | A | 10 | 0.3 | 3 | 99 |
| Example 1 | B | 31 | 2.0 | 20 | 99 |
| Example 2 | C | 50 | 7.3 | 70 | 98 |
| Example 3 | D | 108 | 15.7 | 150 | 99 |
| Example 4 | E | 203 | 11.0 | 110 | 99 |
| Example 5 | F | 404 | 5.3 | 50 | 99 |
| Comparative Example 2 | G | 550 | 3.0 | 30 | 99 |

EXAMPLES 6 TO 10 AND COMPARATIVE EXAMPLES 3 AND 4

Preparation of hydration catalyst

Zeolite Y ("SK-40", Na$_2$O: 7.7%, S/A: 4, a product of Union Showa Co.) was introduced into a quartz tube and was dried in a dry nitrogen stream at 380° C. for 2 hours. After cooling to room temperature, nitrogen saturated (at room temperature) with silicon tetrachloride was fed to the quartz tube at a rate of 250 ml/min for 10 g of zeolite Y. During feeding, the quartz tube was heated at a rate of 4° C./min from room temperature. After the temperature had reached 500° C., the feeding of nitrogen saturated with silicon tetrachloride was continued for 1 hour. The zeolite Y was cooled by feeding nitrogen to the quartz tube, washed with water until chlorine ion was not detected any longer, and finally dried at 200° C. for 8 hours. Thus there was obtained hydrogen-type zeolite Y (catalyst I) containing 0.06% of $Na_2O$ and having an S/A of 29.

Hydrogen-type zeolite Y (Catalyst J) containing 0.05% of $Na_2O$ and having an S/A of 46 was prepared in the same way as for catalyst I, except that the treatment with silicon tetrachloride at 500° C. was extended to 1 hour and 40 minutes.

Hydrogen-type zeolite Y (catalyst K) containing 0.02% of $Na_2O$ and having an S/A of 97 was prepared in the same way as for catalyst I, except that the treatment with silicon tetrachloride at 500° C. was extended to 2 hours and 20 minutes.

Catalyst K was treated with 1N hydrochloric acid (20 cc for 1 g of catalyst K) at 80° C. for 8 hours. The treated catalyst K was washed with water until chlorine ion was not detected any longer and dried at 120° C. Thus there was obtained hydrogen-type zeolite Y (catalyst L) containing 0.01% of $Na_2O$ and having an S/A of 199.

Catalyst L was treated with hydrochloric acid three times and washed and dried in the same way as above. Thus there was obtained hydrogen-type zeolite Y (catalyst M) containing 0.005% of $Na_2O$ and having an S/A of 425.

Catalyst M was treated twice with 1N hydrochloric acid (20 cc for 1 g of catalyst M) at 80° C. for 8 hours. The treated catalyst M was washed with water until chlorine ion was not detected any longer and dried at 120° C. Thus there was obtained hydrogen-type zeolite Y (catalyst N) containing 0.004% of $Na_2O$ and having an S/A of 547.

Zeolite Y as used for the preparation of catalysts was subjected to dealkalization with a 10% aqueous solution of ammonium chloride (15 cc for 1 g of zeolite Y), washed, dried and calcined in the same way as for the preparation of catalyst A in Comparative Example 1. Thus there was obtained hydrogen-type zeolite Y (Catalyst H) containing 0.2% of $Na_2O$ and having an S/A of 4.

The catalysts H to N thus obtained exhibited X-ray diffraction patterns as shown in Table 2. This indicates that they maintain the crystal structure of zeolite Y.

Hydration reaction of olefin

The hydration reaction of 1-butene was carried out in the same way as in Example 2, by using the above catalysts as the hydration catalysts. The results are shown in Table 16.

TABLE 16

| Example No. | Hydration catalysts | | Yield of SBA (mol %) | Space-time yield of SBA (g/l/hr) | Selectivity to SBA (mol %) |
| --- | --- | --- | --- | --- | --- |
| | designation | Silica/alumina (molar ratio) | | | |
| Comparative Example 3 | H | 4 | <0.1 | <1 | — |
| Example 6 | I | 29 | 2.8 | 30 | 99 |
| Example 7 | J | 46 | 7.0 | 70 | 99 |
| Example 8 | K | 97 | 14.9 | 150 | 98 |
| Example 9 | L | 199 | 11.2 | 110 | 98 |
| Example 10 | M | 425 | 5.1 | 50 | 99 |
| Comparative Example 4 | N | 547 | 2.0 | 20 | 99 |

COMPARATIVE EXAMPLE 5

Preparation of hydration catalyst

Crystalline aluminosilicate (ZSM-5) was prepared as follows according to the method described in U.S. Pat. No. 3,965,207. 7.4 parts of aluminum sulfate was dissolved in 195 parts of pure water. To the solution were added 26.5 parts of sulfuric acid, 17.8 parts of tetrapropylammonium bromide, and 86 parts of sodium chloride. Thus there was obtained an aluminum sulfate solution. This aluminum sulfate solution was added with stirring to a mixture of 142 parts of water and 281 parts of water glass ($Na_2O$: 9.5%, $SiO_2$: 28.6%). The resulting mixture was transferred to a stainless autoclave and heated therein with stirring at 160° C. for 20 hours. The crystallized solid product was dried at 110° C. and then calcined at 600° C. for 3 hours. The resulting solid was found to have the crystal structure of ZSM-5 by X-ray analysis.

This ZSM-5 was treated with 1N ammonium chloride aqueous solution at 90° C. for 10 hours, followed by drying at 110° C. and calcination at 600° C. for 3 hours in air. Thus there was obtained hydrogen-type ZSM-5 (HZSM-5) containing 0.01% of $Na_2O$ and having an S/A of 111.

Hydration of olefin

Using the HZSM-5 as a hydration catalyst, the hydration of 1-butene was carried out in the same way as in Example 2. The yield and space-time yield of sec-butanol was 0.8 mol% and 8 g/l-catalyst/hr, respectively.

COMPARATIVE EXAMPLE 6

The hydration of 1-butene was carried out in the same way as in Example 2, by using molecular sieve 10X (calcium X, a product of Union Showa Co.) as a hydration catalyst. The yield of sec-butanol was less than 0.1 mol%.

COMPARATIVE EXAMPLE 7

The hydration of 1-butene was carried out in the same way as in Example 2, by using silica-alumina ("N632-HN", a product of Nikki Co., silica 75% and alumina 25%) as a hydration catalyst. The yield of sec-butanol was less than 0.2 mol%.

COMPARATIVE EXAMPLE 8

Into the autoclave as used in Example 2 were charged 10 ml (6.0 g) of catalyst D, 100 ml of water, and 60 ml (37 g) of 1-butene. Hydration reaction was carried out with stirring at 140° C. for 5 hours. The analysis of the reaction product indicated that the yield, space-time yield, and selectivity to sec-butanol were 5.3 mol%, 50 g/l-catalyst/hr, and 95%, respectively.

COMPARATIVE EXAMPLE 9

Hydration reaction was carried out in the same way as in Comparative Example 8, except that catalyst D was replaced by catalyst J. The yield, space-time yield, and selectivity to sec-butanol were 5.1 mol%, 50 g/l-catalyst/hr, and 96%, respectively.

EXAMPLES 11 TO 17

The hydration reactions of olefins were carried out under different conditions by using different kinds of sulfones and hydration catalysts. The results are shown in Table 17.

Hydration reaction of olefin

TABLE 17

| Example | Olefin** | Sulfone (ml) | Water (ml) | Hydration catalyst | Reaction Temp. (°C.) | Reaction Time (hr) | Alcohol Yield (mol %) | Alcohol Space-time yield (g/l/hr) | Selectivity (mol %) | Product |
|---|---|---|---|---|---|---|---|---|---|---|
| 11 | Ethylene | 2-Methylsulfolane (200) | 100 | L | 210 | 1 | 6.7 | 140 | 99 | 2* |
| 12 | Propylene | Sulfonlane (220) | 80 | E | 160 | 3 | 12.4 | 180 | 98 | 3* |
| 13 | 1-Butene | Dimethylsulfone (240) | 60 | K | 150 | 4 | 16.1 | 160 | 98 | 4* |
| 14 | 2-Butene | Sulfolane (240) | 60 | D | 140 | 5 | 13.3 | 130 | 99 | 4* |
| 15 | 1-Pentene | Diethylsulfone (250) | 50 | J | 130 | 6 | 8.8 | 80 | 98 | 5* |
| 16 | 1-Hexene | Sulfolane (260) | 40 | C | 130 | 6 | 7.5 | 60 | 97 | 6* |
| 17 | Cyclohexene | 3-Methylsulfolane (260) | 40 | D | 130 | 8 | 8.2 | 60 | 98 | 7* |

Note:
**60 ml (liquid)
2* ethanol,
3* isopropanol,
4* sec-butanol,
5* 2-pentanol,
6* 2-hexanol,
7* cyclohexanol.

EXAMPLES 18 TO 23 AND COMPARATIVE EXAMPLES 10 AND 11

Preparation of hydration catalysts

Catalyst A was prepared as described in Comparative Example 1.

Catalyst A was treated with 12N hydrochloric acid (15 cc for 1 g of catalyst A) at 90° C. for 20 hours. The treated catlyst A was washed with water until chlorine ion was not detected any longer, and then dried at 120° C. and finally calcined at 700° C. for 3 hours in air. Thus there was obtained hydrogen-type mordenite containing 0.05% of Na$_2$O and having an S/A of 29. This mordenite is designated as catalyst B'.

Catalyst A was treated with hot air containing 10% of steam at 700° C. for 3 hours and then treated with 12N hydrochloric acid at 90° C. for 3 hours. The treated catalyst A was washed with water, dried, and calcined in the same way as above. Thus there was obtained hydrogen-type mordenite (catalyst C') containing 0.02% of Na$_2$O and having an S/A of 65.

Catalyst A was treated in the same way as in the case of catalyst C', except that the time of treatment with hydrochloric acid was extended from 3 hours to 8 hours. Thus there was obtained hydrogen-type mordenite containing 0.012% of Na$_2$O and having an S/A of 116. This is designated as catalyst D'.

Catalyst D' was repeatedly subjected to steam treatment and acid extraction in the same way as above in order to increase the silica/alumina ratio. Thus there were obtained catalysts E' and H' containing Na$_2$O and having S/A as follows:

Catalyst E' (Na$_2$O: 0.008%, S/A: 194)
Catalyst F' (Na$_2$O: 0.006%, S/A: 286)
Catalyst G' (Na$_2$O: 0.002%, S/A: 420)
Catalyst H' (Na$_2$O: 0.001%, S/A: 560)

The hydration catalysts A to H' prepared as above gave the same X-ray diffraction pattern as shown in Table 1. This indicates that they keep the crystal structure of mordenite.

Into a 500-ml stainless steel autoclave equipped with a stirrer were charged 10 ml (6.0 g) of hydration catalyst C' prepared as described above, 60 ml of water, and 240 ml of γ-butyrolactone, and finally 36 g of 1-butene was forced in under pressure. The hydration reaction was carried out at 140° C., under 40 kg/cm$^2$, for 5 hours. After the reaction was complete, the autoclave was cooled rapidly and unreacted 1-butene was removed. The analysis of the reaction product indicated that sec-butanol (SBA) was formed in a yield of 12.5 mol%. The space-time yield of SBA was 119 g/l-catalyst/hr. The selectivity to SBA was 98.5 mol%, with the formation of a trace amount of sec-butyl ether and octene as by-products.

Using the catalysts obtained as described above, the hydration reaction of 1-butene was carried out in the same way as described above. The results are shown in Table 18.

TABLE 18

| Example No. | Hydration catalysts designation | Silica/alumina (molar ratio) | Yield of SBA (mol %) | Space-time yield of SBA (g/l/hr) | Selectivity to SBA (mol %) |
|---|---|---|---|---|---|
| Comparative Example 10 | A | 10 | 0.8 | 8 | 99.5 |
| Example 18 | B' | 29 | 6.6 | 61 | 99.1 |
| Example 19 | C' | 65 | 12.5 | 119 | 98.5 |
| Example 20 | D' | 116 | 18.6 | 177 | 98.3 |
| Example 21 | E' | 194 | 14.7 | 140 | 98.4 |
| Example 22 | F' | 286 | 8.3 | 79 | 98.8 |
| Example 23 | G' | 420 | 3.1 | 29 | 99.2 |
| Comparative Example 11 | H' | 560 | 0.6 | 6 | 99.3 |

COMPARATIVE EXAMPLE 12

Into the same autoclave as used in Example 18 were charged 10 ml of catalyst E', 300 ml of water, and 36 g of 1-butene, and hydration reaction was carried out with stirring at 140° C. for 5 hours. The yield of SBA was 3.3 mol%, the space-time yield of SBA was 28 g/l/hr, and the selectivity to SBA was 97.5 mol%.

EXAMPLES 24 TO 28 AND COMPARATIVE EXAMPLES 13 AND 14

Preparation of hydration catalysts

Crystalline aluminosilicate (ZSM-5) was prepared as follows according to the method described in U.S. Pat. No. 3,965,207. 52 g of aluminum sulfate was dissolved in 195 g of pure water. To the solution were added 8.4 g of sulfuric acid, 17.8 g of tetrapropylammonium bromide, and 86 g of sodium chloride. Thus there was obtained an aluminum sulfate solution. This aluminum sulfate solution was added with stirring to a mixture of 142 g of water and 281 g of water glass (Na$_2$O: 9.5%, SiO$_2$: 28.6%). The resulting mixture was transferred to a stainless steel autoclave and heated therein with stirring at 160° C. for 20 hours. The crystallized solid product was dried at 110° C. and then calcined at 600° C. for 3 hours. The resulting solid was found to have the crystal structure of ZSM-5 by X-ray analysis. The S/A was 16.

This solid was treated with a 1N ammonium chloride aqueous solution (15 cc for 1 g of solid) at 90° C. for 1 hour and the solution was removed. This treatment was repeated three times. The treated solid was thoroughly washed with water and dried at 110° C. The solid was mixed with alumina powder so that the weight ratio of aluminosilicate to alumina became 70:30. The mixture was formed into pellets, measuring 2 mm by 5 mm. The pellets were dried at 110° C. and then calcined at 600° C. Thus there was obtained a hydration catalyst containing 0.03% of Na$_2$O and having an S/A of 16. This was designated as catalyst I'.

Catalysts J' to O were prepared in the same way as catalyst I', except that the quantities of aluminum sulfate and sulfuric acid were changed as follows:

| Hydration catalyst | J' | K' | L' | M' | N' | O |
|---|---|---|---|---|---|---|
| Aluminum sulfate (g) | 45 | 30 | 14.9 | 9.0 | 4.5 | 1.5 |
| Sulfuric acid (g) | 11.5 | 18.4 | 25.4 | 27.6 | 30.3 | 32.4 |
| Content of Na$_2$O (%) | 0.02 | 0.01 | 0.005 | 0.004 | 0.003 | 0.001 |
| S/A | 22 | 30 | 60 | 98 | 185 | 545 |

Prior to the treatment with an aqueous solution of ammonium chloride, the catalysts were examined by X-ray. Their X-ray diffraction patterns coincided with that of ZSM-5.

Hydration of olefin

Using the hydration catalysts prepared as above, the hydration of 1-butene was carried out in the same way as in Example 18. The results are shown in Table 19.

TABLE 19

| Example No. | Hydration catalysts designation | Silica/alumina (molar ratio) | Yield of SBA (mol %) | Space-time yield of SBA (g/l/hr) | Selectivity to SBA (mol %) |
|---|---|---|---|---|---|
| Comparative Example 13 | I' | 16 | 2.6 | 24 | 99.0 |
| Example 24 | J' | 22 | 10.4 | 99 | 99.3 |
| Example 25 | K' | 30 | 14.1 | 134 | 99.2 |
| Example 26 | L' | 60 | 16.2 | 154 | 99.0 |
| Example 27 | M' | 98 | 15.5 | 145 | 99.1 |
| Example 28 | N' | 185 | 10.6 | 101 | 99.5 |
| Comparative Example 14 | O | 545 | 0.4 | 4 | 99.9 |

COMPARATIVE EXAMPLE 15

The hydration reaction was carried out under the same conditions as in Example 18 except that the charge consisted of 10 ml of catalyst L', 300 ml of water, and 36 g of 1-butene. The yield of SBA was 0.5 mol%; the space-time yield of SBA was 5 g/l/hr.

EXAMPLES 29 AND 30

Preparation of hydration catalysts

Crystalline aluminosilicate was prepared as follows according to the method described in Japanese Patent Laid-open No. 45111/1983. 15.9 g of aluminum sulfate was dissolved in 97 g of pure water. To the solution were added 9.2 g of sulfuric acid and 43.1 g of sodium chloride. Thus there was obtained an aluminum sulfate solution. This aluminum sulfate solution was added with stirring to a mixture of 71 g of water and 140.4 g of water glass (No. 3). The resulting mixture was transferred to a 1-liter stainless steel autoclave and heated therein at 170° C. for 20 hours. The crystallized solid product was washed with water and dried at 110° C. The resulting solid was found to have the X-ray diffraction pattern as shown in Table 14 and to have a composition of 1.02Na$_2$O.Al$_2$O$_3$.30.2SiO$_2$.10.5H$_2$O.

This solid aluminosilicate was treated with an aqueous solution of ammonium chloride, washed with water, and dried in the same way as in the preparation of catalyst I'. The resulting solid was further mixed with alumina, followed by forming, drying, and calcination. Thus there was obtained catalyst P containing 0.02% of Na$_2$O and having an S/A of 30.

Catalyst Q containing 0.01% of Na$_2$O and having an S/A of 95 was prepared in the same way as catalyst P, except that the quantities of aluminum sulfate and sulfuric acid were changed to 4.5 g and 14.1 g, respectively.

Hydration of olefin

Using the hydration catalysts P and Q, the hydration of 1-butene was carried out in the same way as in Example 18. The results are shown in Table 20.

TABLE 20

| Example No. | Hydration catalysts designation | Silica/alumina (molar ratio) | Yield of SBA (mol %) | Space-time yield of SBA (g/l/hr) | Selectivity to SBA (mol %) |
|---|---|---|---|---|---|
| Example 29 | P | 30 | 11.5 | 109 | 99.5 |
| Example 30 | Q | 95 | 5.4 | 51 | 99.8 |

COMPARATIVE EXAMPLE 16

The hydration reaction was carried out under the same conditions as in Example 18 except that the charge consisted of 10 ml of catalyst P, 300 ml of water, and 36 g of 1-butene. The yield of SBA was 0.3 mol%; the space-time yield of SBA was 3 g/l/hr.

EXAMPLES 31 TO 33 AND COMPARATIVE EXAMPLES 17 AND 18

Zeolite Y ("SK-40", Na$_2$O:10.8%, S/A: 4, a product of Union Showa Co.) was treated with a 1N aqueous solution of ammonium chloride (15 cc for 1 g of zeolite) at 90° C. for 1 hour. The solution was removed. This step was repeated three times. The treated zeolite was thoroughly washed with water, dried at 110° C. for 8 hours, and calcined at 600° C. for 3 hours. Thus there was obtained hydrogen-type zeolite Y containing 0.2% of Na$_2$O and having an S/A of 4. This was designated as Catalyst R.

The zeolite Y used in the above step was placed in a quartz tube and was dried in a dry nitrogen stream at 380° C. for 2 hours. After cooling to room temperature, nitrogen saturated (at room temperature) with silicon tetrachloride was fed to the quartz tube at a rate of 280 ml/min for 10 g of zeolite Y. During feeding, the quartz tube was heated at a rate of 4° C./min from room temperature. After the temperature had reached 500° C., the feeding of nitrogen saturated with silicon tetrachloride was continued for 1 hour. The zeolite Y was cooled by feeding nitrogen to the quartz tube, washed with water until chlorine ion was not detected any longer, and finally dried at 200° C. for 8 hours. Thus there was obtained hydrogen-type zeolite Y (catalyst S) containing 0.04% of Na$_2$O and having an S/A of 32.

Hydrogen-type zeolite Y (catalyst T) containing 0.02% of Na$_2$O and having an S/A of 95 was prepared in the same way as catalyst S, except that the treatment with silicon tetrachloride at 500° C. was extended from 1 hour to 2 hours and 15 minutes.

Catalyst T was treated with 1N hydrochloric acid (20 cc for 1 g of catalyst T) at 80° C. for 10 hours. The treated catalyst T was washed with water until chlorine ion was not detected any longer and dried at 120° C. Thus there was obtained hydrogen-type zeolite Y (catalyst U) containing 0.01% of Na$_2$O and having an S/A of 203.

Catalyst T was treated with hydrochloric acid three times and washed and dried in the same way as above. Thus there was obtained hydrogen-type zeolite Y (catalyst V) containing 0.005% of Na$_2$O and having an S/A of 524.

The catalysts R to V obtained as described above exhibited X-ray diffraction patterns as shown in Table 2. This indicates that they maintain the crystal structure of zeolite Y.

Hydration reaction of olefin

The hydration reaction of 1-butene was carried out in the same way as in Example 18, by using the above catalysts R to V. The results are shown in Table 21.

TABLE 21

| Example No. | Hydration catalysts designation | Silica/alumina (molar ratio) | Yield of SBA (mol %) | Space-time yield of SBA (g/l/hr) | Selectivity to SBA (mol %) |
|---|---|---|---|---|---|
| Comparative Example 17 | R | 4 | 0.1 | 1 | — |
| Example 31 | S | 32 | 4.3 | 39 | 98.5 |
| Example 32 | T | 95 | 15.6 | 148 | 98.0 |
| Example 33 | U | 203 | 11.8 | 109 | 98.5 |
| Comparative Example 18 | V | 524 | 0.5 | 5 | 99.0 |

COMPARATIVE EXAMPLE 19

The hydration of 1-butene was carried out in the same way as in Example 18, by using silica-alumina ("632-NH", a product of Nikki Co., S/A:5.1) as a hydration catalyst. The yield of SBA was only 0.1 mol%.

COMPARATIVE EXAMPLE 20

Into the same autoclave as used in Example 19 were charged 100 ml of water, 100 ml of γ-butyrolactone, 100 ml of liquefied 1-butene, and 3.5 g of cation-exchange resin composed of sulfonated styrenedivinyl benzene copolymer (having an exchange capacity of 4.5 milliequivalent/g, containing 14.98% of sulfur, and having a surface area of 34 m$^2$/g) as a catalyst. The hydration of 1-butene was carried out at 140° C. for 8 hours. The yield, space-time yield, and selectivity to SBA were 10.4 mol%, 101 g/l-catalyst/hr, and 96.5 mol%, respectively. By-products were di-sec-butyl ether and octene.

After the reaction, the cation-exchange resin was washed with water and dried, the composition was analyzed and the exchange capacity was measured. The sulfur content was 11.98% and the exchange capacity was 3.5 milliequivalents/g. This indicates that sulfonic acid groups dropped off from the cation-exchange resin.

EXAMPLES 34 TO 40

The hydration reaction of olefines were carried out in the same autoclave as used in Example 18 under different conditions by using the hydration catalysts (10 ml each) prepared as described above. The results are shown in Table 22.

TABLE 22

| Example | Olefin (ml)** | Oxyacid or Derivative thereof (ml) | Water (ml) | Hydration catalyst | Reaction Temp. (°C.) | Time (hr) | Alcohol Yield (mol %) | Space-time yield (g/l/hr) | Selectivity (mol %) | Product |
|---|---|---|---|---|---|---|---|---|---|---|
| 34 | Propylene (60) | γ-Butyrolactone (240) | 60 | P | 160 | 4 | 13.5 | 168 | 98 | 2* |
| 35 | 1-Butene (100) | α-Valerolactone (100) | 100 | E' | 150 | 8 | 15.1 | 145 | 97 | 3* |
| 36 | 1-Butene (60) | γ-Hydroxybutyric acid (250) | 50 | C' | 140 | 5 | 12.6 | 120 | 97 | 3* |
| 37 | 2-Butene (60) | γ-Valerolactone (200) | 100 | D' | 140 | 5 | 16.8 | 160 | 97 | 3* |
| 38 | 2-Butene (60) | β-Propiolactone (240) | 60 | L' | 140 | 6 | 17.2 | 138 | 98 | 3* |
| 39 | 1-Hexene (80) | 3-Hydroxypropionic acid (240) | 50 | D' | 130 | 6 | 8.0 | 85 | 97 | 4 |
| 40 | Cyclohexene | γ-Butyrolactone | 100 | E' | 140 | 7 | 7.2 | 59 | 97 | 5* |

TABLE 22-continued

| Example | Olefin (ml)** | Oxyacid or Derivative thereof (ml) | Water (ml) | Hydration catalyst | Reaction Temp. (°C.) | Time (hr) | Yield (mol %) | Alcohol Space-time yield (g/l/hr) | Selectivity (mol %) | Product |
|---|---|---|---|---|---|---|---|---|---|---|
| | (60) | (200) | | | | | | | | |

Note:
**(liquid)
2* isopropanol,
3* sec-butanol,
4* 2-hexanol,
5* cyclohexanol.

What is claimed is:

1. An improved process for producing an alcohol by hydrating an olefin wherein the improvement comprises hydrating an olefin in the presence of a hydrogen-type catalyst having a silica/alumina molar ratio of 20 to 500 and a solvent using either:
   A. hydrogen-type mordenite or hydrogen-type zeolite Y, and a sulfone; or
   B. hydrogen-type crystalline aluminosilicate in which the entrance of the main void is formed by a 10-membered or 12-membered oxygen ring, and a $C_2$ to $C_5$ oxy acid or the lactones, lactides, methyl or ethyl esters thereof.

2. An improved process for producing an alcohol by hydrating an olefin, wherein the improvement comprises hydrating an olefin in the presence of hydrogen-type mordenite or hydrogen-type zeolite Y as a catalyst each having a silica/alumina molar ratio of 20 to 500, and a sulfone.

3. An improved process for producing an alcohol by hydrating an olefin, wherein the improvement comprises hydrating an olefin in the presence of hydrogen-type crystallline aluminosilicate as a catalyst in which the entrance of the main void is formed by a 10-membered or 12-membered oxygen ring and the silica/alumina molar ratio is 20 to 500, and a $C_2$ to $C_5$ oxy acid or the lactones, lactides, methyl or ethyl esters thereof.

4. The process according to claim 3 in which the catalyst is prepared from a crystalline aluminosilicate selected from the group consisting of ZSM-4, ZSM-5, ZSM-10, ZSM-11, ZSM-12, ZSM-20, ZSM-23, ZSM-35, ZSM-38 and ZSM-43.

5. The process according to claim 2 in which the catalyst has a silica/alumina molar ratio in the range of 30 to 400.

6. The process according to claim 2 in which said hydrogen-type mordenite is obtained by dealkalization, acid extraction and steam treatment of mordenite.

7. The process according to claim 2 in which said hydrogen-type mordenite is obtained by acid extraction and steam treatment of mordenite.

8. The process according to claim 2 in which said hydrogen-type zeolite Y is obtained by removing by extraction alkali metal or alkaline earth metal and alumina from zeolite Y.

9. The process according to claim 8 in which the dealkalization and removal of alumina are accomplished by bringing zeolite Y into contact with silicon tetrachloride.

10. The process according to claim 1 in which the olefin has from 2 to 12 carbon atoms.

11. The process according to claim 10 in which the olefin has from 2 to 8 carbon atoms.

12. The process according to claim 11 in which the olefin is aliphatic having from 2 to 6 carbon atoms, or is cyclohexene.

13. The process according to claim 1 in which isopropanol is produced from propylene or sec-butanol is produced from 1-butene or 2-butene.

14. The process according to claim 12 in which the reaction temperature is in the range of 130° to 210° C.

* * * * *